United States Patent [19]

Chang

[11] Patent Number: 4,950,279

[45] Date of Patent: Aug. 21, 1990

[54] ACUPUNCTURE DELIVERY SYSTEM

[75] Inventor: William Chang, Monterey Park, Calif.

[73] Assignee: Jen-On Pharmaceutical Enterprises Corp., Monterrey Park, Calif.

[21] Appl. No.: 333,132

[22] Filed: Apr. 3, 1989

[51] Int. Cl.$^5$ .............................................. A61B 17/34
[52] U.S. Cl. ...................................................... 606/189
[58] Field of Search ............... 606/167, 170, 185, 188, 606/189

[56] References Cited

U.S. PATENT DOCUMENTS

| | | | |
|---|---|---|---|
| 3,861,392 | 1/1975 | Moen | 606/189 |
| 3,905,375 | 9/1975 | Toyama | 606/189 |
| 3,976,078 | 8/1976 | Toriello | 606/189 |
| 4,161,943 | 7/1979 | Nogier | 606/189 X |
| 4,262,672 | 4/1981 | Kief | 606/189 |
| 4,479,496 | 10/1984 | Hsu | 606/189 |

*Primary Examiner*—Robert A. Hafer
*Assistant Examiner*—Lynda M. Cofsky
*Attorney, Agent, or Firm*—Ashen Golant Martin & Seldon

[57] ABSTRACT

An acupuncture needle delivery system is disclosed comprising a needle with an upper head portion that is wider in the middle than at its ends. The needle is packaged within a plastic dispensing tube which is greater in diameter than the needle, except at the end of the tube which surrounds the needle's head. The portion of the tube surrounding the head of the needle is narrower than the widest part of the head to snugly grasp the head and secure the needle within the tube. Upon the imposition of axially directed, manually exerted, downward pressure on the head region, the end of the plastic tube stretches, permitting the needle to be ejected from the other end of the tube.

7 Claims, 1 Drawing Sheet

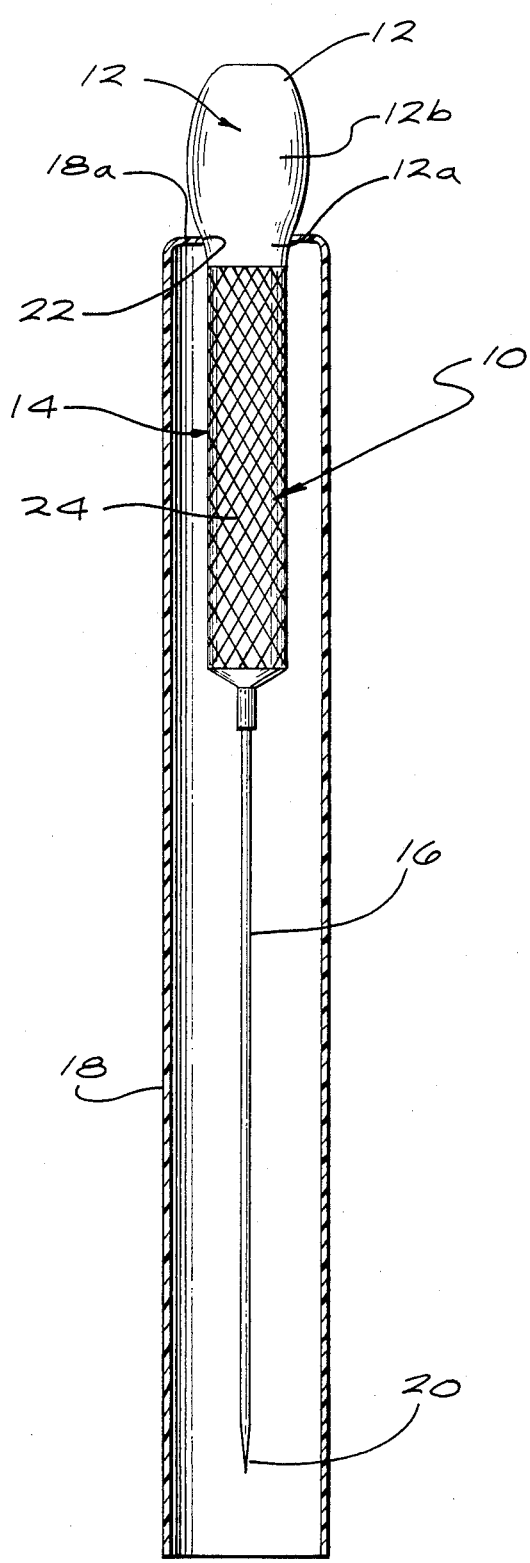

ACUPUNCTURE DELIVERY SYSTEM

This invention relates to medical devices and, more specifically, to an acupuncture needle delivery system.

In the practice of acupuncture, it has become increasingly desirable to use disposable needles which are sterilized prior to packaging in order to avoid the potential use of contamined needles. Additionally, for the same reason, a number of different delivery systems have been marketed for inserting the needle into the body part of the patient without the need for the practitioner to touch the body of the needle.

Acupuncture needles comprise a head portion at the top of the structure, a handle portion which is grasped by the practitioner's fingers after insertion of the needle for rotational movement of the inserted needle, and a body portion which terminates in a leading pointed tip designed to penetrate the patient's skin.

A number of known delivery systems utilize a plastic tube which surrounds the handle and body portions of the needle so that only the head protrudes. The tube is of a larger cross-section than the head of the needle to allow the passage of the head through the tube. One delivery system simply utilizes a paper wedge between the needle and tube to prevent the needle from slipping through the tube. The wedge is removed just prior to use, and the needle is pressed through the patient's skin as the tube is pressed against the surrounding area of the skin. However, the needle can accidentally slip out of the tube and drop to the floor or otherwise become contaminated, because the paper wedge either does not securely affix the needle to the tube, or the wedge has become displaced during handling.

In another delivery system, the position of the needle within the tube is maintained by a helical spring which is wound around both the head of the needle and the top of the tube so that, by snugly spanning the two structures, the spring prevents the needle from falling through the tube. By pressing downward on the head of the needle, the practitioner causes the helical spring to compress and distort outwardly, permitting the needle to fall through the tube. If the bottom of the tube is pressed against the patient's body part at the time the needle head is pressed, the momentum of the needle is sufficient to cause the pointed tip of the needle to pierce the patients skin while the pressure of the tube's bottom edge masks the sensation of the needle.

In practice it has been found that reliable and consistent action is not obtained by the pressing of the needle's head. In some cases, the spring does not release the head as intended, but appears to interfere with the crisp releasing movement which is highly desirable. Conversely, the resiliency of the spring has sometimes resulted in the needle being accidentally released during handling of the assembly. This can not only lead to a mis-insertion or non-insertion of the needle, but can also cause the patient pain as the needle incorrectly penetrates the skin. In addition, the needle must then be disposed of and a new assembly utilized.

SUMMARY OF THE INVENTION

An acupuncture needle delivery system is disclosed comprising an axially extending needle having an upper head portion, a middle handle portion and a relatively slender lower body portion terminating in a leading point. The mid-portion of the head portion is slightly larger in cross-section than the end portions of the head portion.

The needle is packaged within a plastic tube having an inner diameter along substantially its entire length which is greater than any portion of the needle. The end of the plastic tube adjacent the head of the needle has a slightly lesser cross-section than the widest part of the head region, but is slightly greater in cross section than the end portions of the head region. The needle is mounted within the tube for discharge therefrom, with its head region snugly grasped within said adjacent end of the tube.

The widest cross-section of the head portion is within the limits to which the surrounding grasping end of the plastic tubing will expand upon the imposition of axially directed, manually exerted, downward pressure on the head region, whereby the needle is ejected from the other end of the tube.

Accordingly, as desribed in greater detail below, the delivery system provides an economical, reliable structure with a minimum number of parts. These and other features of the invention are described in detail in the following Description of the Preferred Embodiment, of which the sole Figure is a part.

DESCRIPTION OF THE DRAWING

The FIGURE is an elevation view of an acupuncture needle and delivery system constructed in accordance with the invention .

DESCRIPTION OF THE PREFERRED EMBODIMENT

Referring to the FIGURE, an elevation view of an acupuncture needle and delivery system is shown which is constructed in accordance with the invention. The needle 10 has a head portion 12 approximately 8 mm in axial length, a 1.5 mm diameter handle portion 14 approximately 22 mm in axial length, and a body portion 16 having an axial length which depends on the intended use for the needle. Typical lengths are from 0.5 to 3.0 inches, in 0.5 inch increments. The head and handle portions of the needle are preferably made from aluminum, while the body portion is preferably made from stainless steel.

The needle is mounted within a plastic dispensing tube 18 having a 2.0 mm inner diameter, and a length which depends on the length of the encased needle. The tube 18 preferably extends approximately 1.5 mm beyond the tip 20 of the encased needle and is open-ended thereat.

The head portion 12 of the needle has a bowed configuration, with its mid-region 12b being wider than its end regions 12a. In practice, a diameter of approximately 1.8 mm at the widest part and 1.7 mm at the two ends has been employed.

The upper end 18a of the tube 18 is close-ended, with a circumferential lip means defining a 1.7 mm through-hole 22. Alternatively, the end 18a of the tube can be deformed slightly inward from its non-deformed diameter to the 1.7 mm dimension. The hole 22 snugly circumscribes the bottom end of the head 12 and, by grasping the head 12, retains the needle 10 within the tube.

Because of the slight elasticity of the plastic forming the tube 18, the hole 22 expands enough to permit the head to be pushed through by an axially directed, manually exerted, downward force. Once the widest portion of the head 12 passes through the hole 22, the needle falls freely through the tube and penetrates the patient's skin. The necessity for a positive force against the head minimizes the chance for accidental release which occurs with the spring-type of delivery system described hereinabove. In addition, the releasing action is crisp and controllable.

Using the aforedescribed delivery system, the needle can be inserted into the patient's body with one hand, and the risk of contamination to the needle during the insertion process is minimal. The tube 18 is simply held between the practitioner's thumb and middle finger, and pressed down against the patient's body. The head of the needle is then pressed downward with the practitioner's index finger to release the needle. Consequently, even needles longer than two inches, which have been difficult to insert with one hand in the past, are easily and precisely placed in the patient.

In accordance with the invention, the handle portion 14 of the needle is provided with a "pineapple" pattern of surface indentations 24. It has been found that the illustrated pattern yields a greater tactile sensation which enables the practitioner to rotate the needle and/or further penetrate the body member with more ease and precision. Naturally, the indentations could, instead, be raised above the surface of the handle portion. All that is needed to accomplish the function is a pattern of criss-crossing lines which are non-planer with the surface of the handle portion and which extend at an oblique angle with respect to the needle axis.

While the foregoing description includes detail which will enable those skilled in the art to practice the invention, it should be recognized that the description is illustrative in nature and that many modifications and variations will be apparent to those skilled in the art having the benefit of these teachings. It is accordingly intended that the invention herein be defined solely by the claims appended hereto and that the claims be interpreted as broadly as permitted in light of the prior art.

I claim:

1. An acupuncture needle delivery system comprising:

an axially extending needle having an upper head portion, having a mid-portion a middle handle portion and a relatively slender lower body portion terminating in a leading point, the mid-portion of the head portion being slightly larger in cross-section than the end portions of the head portion, a deformable plastic tube having a first and a second end portions and a tube body disposed therebetween, said tube body having an inner diameter along substantially its entire length which is greater than any portion of the needle, the first end portion of the plastic tube being open and the second end portion having a circumferential lip means disposed thereon, said circumferential lip means defining a through-hole of a slightly lesser cross-section than the widest part of the head region, the needle being mounted within the tube for discharge therefrom, with its head region snugly grasped within said second end portion of the tube, the widest cross-section of the head portion being within the limits to which the circumferential lip means of the plastic tubing will expand upon the imposition of axially directed, manually exerted, downward pressure on the head region, whereby the needle is ejected from the other end of the tube.

2. The system of claim 1 wherein the axial length of the tube is sufficient to extend at least to the leading edge of the needle's tapered point.

3. The system of claim 1 wherein the difference is cross section between the mid-portion and end portion of the head portion is approximately 1-2 mm.

4. The system of claim 3 wherein the mid portion of the head portion is approximately 1.8 mm in cross section.

5. The system of claim 3 wherein the tube is approximately 2.0 mm internal in cross section along substantially its entire length.

6. The system of claim 5 wherein said one end of the tube is approximately 1.7 mm in internal cross-section.

7. The system of claim 1 wherein the handle portion of the needle has pineapple-like pattern of criss-crossing lines which are non-planer with the surface of the handle portion and which extend at an oblique angle with respect to the needle axis.

* * * * *